United States Patent [19]
Ondetti

[11] 3,947,575
[45] Mar. 30, 1976

[54] PEPTIDES AS ARGIOTENSIN CONVERTING ENZYME INHIBITORS

[75] Inventor: Miguel A. Ondetti, Princeton, N.J.

[73] Assignee: E. R. Squibb & Sons, Inc., Princeton, N.J.

[22] Filed: June 21, 1974

[21] Appl. No.: 481,615

Related U.S. Application Data

[63] Continuation-in-part of Ser. Nos. 837,888, June 30, 1969, abandoned, and Ser. No. 182,560, Sept. 21, 1971, Pat. No. 3,819,831.

[52] U.S. Cl............. 424/177; 424/98; 260/112.5 R
[51] Int. Cl.² ........................................ A61K 37/00
[58] Field of Search............................ 424/98, 177

[56] References Cited
UNITED STATES PATENTS

| | | | |
|---|---|---|---|
| 3,819,831 | 6/1974 | Ondetti | 424/98 |
| 3,832,337 | 8/1974 | Ondetti et al. | 424/177 |

OTHER PUBLICATIONS

Chemical Abstracts, Vol. 41, (1947), p. 6994h.

*Primary Examiner*—V. D. Turner
*Attorney, Agent, or Firm*—Lawrence S. Levinson; Merle J. Smith; Burton Rodney

[57] ABSTRACT

Disclosed herein is a process for the utilization of certain peptides as angiotensin converting enzyme inhibitors.

5 Claims, No Drawings

PEPTIDES AS ARGIOTENSIN CONVERTING ENZYME INHIBITORS

RELATED APPLICATIONS

The present application is a continuation-in-part of copending application Ser. No. 837,888, filed June 30, 1969, now abandoned and of copending application Ser. No. 182,560, filed Sept. 21, 1971 now U.S. Pat. No. 3,819,831.

SUMMARY OF THE INVENTION

This invention relates to the utilization of peptides as inhibitors for the conversion of a decapeptide (angiotensin I) to an octapeptide (angiotensin II).

BACKGROUND OF THE INVENTION

More and more, scientific evidence is being compiled to establish that the angiotensin II, an octapeptide, causes hypertension. This peptide is formed from a precursor decapeptide angiotensin I which is produced by the action of the enzyme renin on a substrate material known as angiotensinogen. It has now been discovered that certain peptides can inhibit the formation of angiotensin II from angiotensin I.

DETAILED DESCRIPTION

The peptides of the present invention may be obtained from snake venom. Crude snake venom is processed and suspended in an alcoholic solution. This solution is then fractionated by passing it through a molecular sieve of the gel type. The bioactivity of each fraction from gel filtration is then determined and each bio-active fraction then further fractionated first through a cation exchanger and thereafter through an anion exchanger. The bio-active fractions recovered by this latter fractionation are then subjected to partition and-/or adsorption chromatography.

The fractionating procedures are carried out utilizing known techniques so as to collect those fractions which have U.V. absorption of from about 235 to about 300 m$\mu$, and to subject them to a bio-assay to determine their activity as angiotensin II inhibitors. Any suitable bio-assay test may be employed. Fractions showing the lowest $I_{50}$ are chosen for further fractionation and processing. One suitable test is that described in "A Simple Substrate for the Assay of Dog Lung Angiotensin Converting Enzyme," by D. W. Cushman and H. S. Cheung, FEDERATION PROCEEDINGS, 28, 799 (1969). Another is "Conversion of Angiotensin I to Angiotensin II by Cell-Free Extracts of Dog Lung," by Y. S. Bakhle, NATURE, 220, 919. Still another is that described in an article entitled "Spectrophotomatic Assay and Properties of Angiotensin-Converting Enzyme of Rabbit Lung," by D. W. Cushman and H. S. Cheung, BIOCHEMICAL PHARMACOLOGY, 20, 1637 (1971). After the fractions from gel filtration are recovered, the two which show the greatest activity are then fractionated through a cation exchange resin followed by recovery of the various fractions as stated above and testing of each fraction for bio-activity.

The fractions that show the best activity—that is, the lowest $I_{50}$—are then individually fractionated by partition and exchange chromatography to obtain the final active fractions of this invention. The $I_{50}$ is that concentration of peptides expressed in micrograms per ml, required to inhibit 50% of the activity of the angiotensin-converting enzyme. Following the procedure outlined, three bio-active fractions are recovered, labelled for purposes of convenience as Sheilacin, Jamacin, and Deanacin.

The final fractions of the invention which show high activity as inhiibitors in the formation of angiotensin II from angiotensin I are peptides. The peptides fractions can be identified by their chemical characteristics, e.g., paper chromatography, paper electrophoresis and amino acid compositions as established in the examples.

The alcoholic solution of crude *Bothrops jararaca* is prepared by first suspending 1 part of the snake venom in from about 5 parts to about 200 parts by weight of water and heating at a point below 100°C, preferably from between 85° to 98°C for about 5 to about 30 minutes. The aqueous suspension is diluted with from about 5 to about 10 volumes of alcohol, filtered and washed. This procedure is preferred; however, other known methods of preparing an alcoholic extract of venom may be utilized.

The filtrate is concentrated in vacuo and the residue is passed through any molecular sieve which will fractionate peptides having a molecular weight of from about 200 to about 5,000 with the most preferred molecular sieves being those that extract peptides having molecular weights from about 200 to about 2,600. The molecular sieves are gel filtration agents composed of modified dextrans crosslinked to give a 3-dimensional network of polysaccharide, or of polyacrylamides. They are available in the form of beads or spheres having a diameter of from 40 to 150 microns. Suitable molecular gel sieves are, for example, Sephadex G-25, Sephadex G-15, Bio-Gel P-2, and Bio-Gel P-4. Sephadex G25 is a modified dextranmolecular sieve in the form of beads having a diameter of from 50–150 microns and which is capable of fractionating compounds with a molecular weight between 1,000 and 5,000. Sephadex G-15 is a modified dextran molecular sieve in the form of beads having a diameter of from 40–120 microns and which is capable of fractionating compounds with a molecular weight up to 1,500. Bio-Gel P-2 is a spherical polyacrylamide gel suitable for the separation of molecules with a molecular weight up to 1,800. Bio-Gel P-4 is a spherical polyacrylamide gel suitable for the separation of molecules with a molecular weight up to 4,000.

The eluate from the molecular sieve is tested for angiotensin-converting inhibition and the active fractions are passed through a cation exchange resin, e.g., carboxymethyl cellulose; Dowex 50W; Amberlite IRC-50; Amberlite IR-120, and the like. It is to be understood, however, that any cation exchange resin which will fractionate peptides on the basis of their net positive charge may be employed. Dowex 50-W and Amberlite IR-120 are synthetic cation exchange resins consisting of an ionizable sulfonic acid residue attached to an insoluble styrenedivinylbenzene, while Amberlite IRC-50 is a weakly acidic cation exchange resin of the acrylic type.

The eluate from the cation exchange resin is tested for angiotensin-converting inhibition and the active fractions are then passed through an anion exchange resin, e.g., DEAE Sephadex; DEAE Cellulose; Dowex 1, Amberlite IR-4B; Amberlite IRA 400, and the like. It is to be understood, however, that any anion exchange resin which will fractionate peptides on the basis of their net negative charge may be employed. DEAE Sephadex is a modified dextran anion exchange resin to which diethylaminoethyl functional groups have been attached, while DEAE Cellulose is a cellulose anion exchange resin to which diethylaminoethyl functional groups have been attached. Dowex 1 and Amberlite IRA 400 ae strongly basic synthetic anion exchange resins consisting of a quaternary ammonium ionizable group attached to a styrenedivinylbenzene matrix, while Amberlite IR-4B is a weakly basic synthetic ion exchange resin of the polystyrene type.

After passing the active fractions through an anion exchange resin, the two active fractions having the lowest $I_{50}$ are selected for further processing. One fraction is subjected to partition chromatography to yield Jamacin and Deanacin and the other fraction is subjected to absorption chromatography to yield an active fraction called Sheilacin.

Each of these fractions can be formulated in injectable form so the active ingredient is from 0.1 to 10 mg per kg of body weight, the preferred dose range being from 1 to 5 mg per kg of body weight to be administered to mammaliam host in four equal injections over the period of twenty-four hours.

A preferred peptide of the present invention, that of example 6, has been identified chemically as L-pyroglutamyl-L-tryptophyl-L-prolyl-L-arginyl-L-prolyl-L-glutaminyl-L-isoleucyl-L-prolyl-L-proline. This peptide can also be produced by chemical synthesis. This peptide effectively inhibits the enzymatic conversion of angiotensin I into angiotensin II when employed at a concentration of from about 0.05 to about 10 μg/ml, or inhibits the hypertensive effect of angiotensin I in mammalian species, e.g., rats and dogs, when administered in a dosage level of from about 0.025 to about 4 mg/kg.

The peptides of the present invention may be administered intramuscularly, subcutaneously or intravenously. For such use the peptide in lyophilized form may be reconstituted with saline or water for injection. Various other pharmaceutically acceptable materials such as carriers, diluents, preservatives, e.g., methyl and propyl parabens, may also be incorporated into the reconstituted peptide.

The following examples are illustrative of the invention. All temperatures are in degrees Centigrade unless otherwise stated. The $I_{50}$ in Examples 2 and 3 is measured according to the procedure of Cushman et al., FEDERATION PROCEEDINGS, supra. The designation "NI" in these examples indicates "No Inihibition."

Paper electrophoresis tests are run on Whatman No. 4 with a voltage gradient of 10–20 volt/cm for a period of 30 to 180 minutes. Organic buffers containing 30% formamide are used. Mobilities are measured relative to a set of reference dyes (Apolon: 4[4'](2-hydroxyethyl)-phenylazo]-2'',2'''-(phenyl-imino)-diethanol; Amaranth: trisodium salt of 1-(4-sulfo-1-naphthylazo)-2-naphthol-3,6-disulfonic acid). The mobility of any compound in Am units is obtained by measuring the distance of the spot to the Apolon spot, dividing by the Amaranth-Apolon distance and multiplying by 100. The charge on the compound is indicated by a minus sign if it has moved in the same direction as Amaranth.

EXAMPLE 1

Preparation of Crude Alcoholic Snake Venom Extract

Crude *Bothrops jararaca* venom (10 grams) is thoroughly suspended in water (1 liter) and heated for 15 minutes in a 97°C water bath. After cooling to ambient temperature and diluting with 7500 ml of absolute ethanol, the suspension is filtered through a Celite pad and the filtrate concentrated under vacuum to dryness. The residue is dissolved in water and freeze-dried. The solid residue is extracted with 90% ethanol several times (total volume 400 ml.). The combined ethanol extracts are diluted with 2 liters of ethyl ether. The precipitate formed is collected by centrifugation, dissolved in water (100 ml.) and freeze-dried. Yield 642 mg. The foregoing procedure is repeated to obtain additional crude extract.

EXAMPLE 2

Fractionation on Molecular Gel Sieve

Sephadex G-25 (360 g.) is suspended in 4 l. of 0.2 M acetic acid and allowed to swell for 3 hours. After 30 minutes deaeration in vacuo the slurry is poured into a column (5 cm diameter, 100 cm high) containing a small amount of 0.2 M acetic acid. The crude alcoholic extract of venom (1.3 g) from Example 1 is dissolved in 0.2 M acetic acid (10 ml) and applied to the top of the column. Elution is carried out with 0.2 M acetic acid. On the basis of the UV absorption at 280 mμ, eleven pooled fractions are obtained which on removal of solvent yield the following quantities of solids:

| | | | $I_{50}$ (in vitro) |
|---|---|---|---|
| Fraction | 1 | 96 mg | 6.1 μg/ml |
| | 2 | 334 } | 5.4 μg/ml |
| | 3 | 182 } | |
| | 4 | 219 | N I |
| | 5 | 60 | N I |
| | 6 | 14 | N I |
| | 7 | 69 | 5.6 μg/ml |
| | 8 | 49 | N I |
| | 9 | 0 | |
| | 10 | 95 | N I |
| | 11 | 2 | |

EXAMPLE 3

Fractionation on Cation Exchanger

Carboxymethylcellulose (Whatman CM-52) (100 g) is suspended in 4 l. of 0.005 M ammmonium acetate and allowed to stand ca. 20 minutes. The supernatant is decanted and the washing repeated 6 times in the same way. After deaeration a column is packed and washed with 0.005 M ammonium acetate. Fractions 2 and 3 from the Sephadex G-25 fractionation (516 mg) are combined and dissolved in 0.005 M ammonium acetate (5 ml) and applied to the top of the column. Elution is carried out with 0.005 M ammonium acetate and is monitored by UV absorption. All the tubes showing a significant UV absorption at 280 mμ are pooled, concentrated to dryness and freeze-dried. Yield 437 mg (Fraction 1*a*). The column is then washed with 0.2 M acetic acid and the material thus eluted is recovered by freeze-drying the solvent. Yield: 25 mg (Fraction 2*a*). This latter fraction is not utilized for further testing.

EXAMPLE 4

Fractionation on DEAE-Sephadex

DEAE-Sephadex (100 ml) in the OH cycle is washed with 0.005 M ammonium bicarbonate (5 × 400 ml) and placed in a column (15 cm diameter-24 cm length) after deaeration. The major portion of Fraction 1*a*from the CMC fractionation (417 mg) of Example 3 is dissolved in 0.005 M ammonium bicarbonate (5 ml) and applied to the top of the column. Elution is carried out with a linear gradient of ammonium bicarbonate (from 900 ml of 0.005 M and 900 ml of 1 M). The elution is monitored by UV absorption. Twelve pooled fractions are obtained showing significant UV absorption at 280 mμ which on removal of solvent yield the following quantities of solids:

| Fraction | | | $I_{50}$ (in vitro) |
|---|---|---|---|
| | 1b | 69 mg | 5 μg/ml |
| | 2b | 8 | 20 μg/ml |
| | 3b | 23 | N I |
| | 4b | 39 | 0.6 μg/ml |
| | 5b | 48 | 2.3 μg/ml |
| | 6b | 8 | 10.4 μg/ml |
| | 7b | 26 | N I |
| | 8b | 10 | N I |
| | 9b | 75 | N I |
| | 10b | 75 | N I |
| | 11b | 33 | N I |
| | 12b | 2 | |

EXAMPLE 5

Fractionation on Silica Gel

Fraction 5b from Example 4 (10 mg) is applied to a thin layer plate of silica gel (20 × 20 cm) in a streak 17 cm wide and the plate run with methanol. After the solvent front has traveled a distance of approximately 18 cm, the plate is dried and observed under UV light. Two distinct bands [$R_f$ 0.42 - Fraction 1c); $R_f$ 0.17 (Fraction 2c)] are observed. The silica gel with each band is removed and washed with methanol. The solvent is evaporated to dryness. Yield Fraction 1c: ($I_{50}$- 0.9 μg/ml); Fraction 2c: 3.9 mg ($I_{50}$:22 μg/ml).

Analysis of 1c called Sheilacin for convenience is as follows:

Paper chromatography: Whatman paper 3 MM; descendent; $R_f$ - 0.58; solvent: n-butanol, pyridine, acetic acid, water (30:20:6:24)

Reactions of the chromatographic spots with specific reagents being:

| Ninhydrin | — | Ehrlich | — | Sakaguchi | — | Pauly |
|---|---|---|---|---|---|---|
| Neg. | | Pos. | | Neg. | | Pos. | having an amino acid composition of:

| Amino Acid | (μmoles/mg) |
|---|---|
| Aspartic Acid | 0.9 |
| Serine | 0.5 |
| Glutamic Acid | 1.7 |
| Proline | 2.8 |
| Glycine | 0.3 |
| Isoleucine | 0.6 |
| Ammonia | 2.0 |
| Tryptophan | 0.6* |
| Histidine | 0.6 |

*Determined by UV absorption.

Paper Electrophoresis: According to the technique described in: L. N. Werum, H. T. Gordon, and W. Thornburg, J. Chromatog. 3, 125 (1960):

| pH | AM Values |
|---|---|
| 3.3 | +12 |
| 4.7 | 0 |
| 7.2 | −12 |
| 8.0 | −17 |
| 9.3 | −20 |

EXAMPLE 6

Fractionation by Partition Chromatography

Sephadex G-25 (50 g) is allowed to swell in a mixture of n-butanol-pyridine-acetic acid-water (30:20:6:24) (500 ml) for 3 hours. The suspension is deaerated and poured into a column of 1.5 cm diameter and 95 cm length. Fraction 1b from DEAE-Sephadex fractionation is dissolved in 1 ml of the solvent mixture, and applied at the top of the column. The elution is carried outt with the same solvent system and the 3 ml fractions are scanned by Ehrlich reaction. Two bands with $R_f$ 0.66 (Fraction 1) ($I_{50}$=5 μg/ml) and 0.53 (Fraction 2d) ($I_{50}$=3 μg/ml) are observed, called Jamacin and Deanacin, respectively, for convenience.

These products have the following characteristics:

Jamacin: Paper chromatography: As set forth in Example 5; $R_f$ - 0.66; Reactions of the chromatograph spots with reagents being:

| Ninhydrin | — | Ehrlich | — | Sakaguchi | — | Pauly |
|---|---|---|---|---|---|---|
| Neg. | | Pos. | | Pos. | | Neg. | having an amino acid composition of:

| Amino Acid | (μmoles/mg) |
|---|---|
| Threonine | 0.5 |
| Serine | — |
| Glutamic Acid | 1.1 |
| Proline | 2.6 |
| Glycine | 0.1 |
| Isoleucine | 0.6 |
| Ammonia | 0.8 |
| Tryptophan | 0.5 |
| Arginine | 0.5 |

Paper Electrophoresis: According to the technique set forth in Example 5:

| pH | AM Values |
|---|---|
| 3.3 | +11 |
| 4.7 | + 1 |
| 7.2 | − 2 |
| 8.0 | − 4 |
| 9.3 | − 4 |

Deanacin: Paper chromatography: As described in Example 5; $R_f$: 0.53 Reactions of the chromatographic or electrophoretic spots being:

| Ninhydrin | — | Ehrlich | — | Sakaguchi | — | Pauly |
|---|---|---|---|---|---|---|
| Neg. | | Pos. | | Pos. | | Neg. | having an amino acid composition of:

| Amino Acid | (μmoles/mg) |
|---|---|
| Glutamic Acid | 1.2 |
| Proline | 2.2 |
| Isoleucine | 0.6 |
| Ammonia | 1.8 |
| Tryptophan | 0.5* |
| Arginine | 0.6 |

*Determined by UV absorption

Paper Electrophoresis: According to the technique set forth in Example 5:

| pH | AM Values |
| --- | --- |
| 3.3 | +11 |
| 4.7 | +1 |
| 7.2 | −2 |
| 8.0 | −4 |
| 9.3 | −4 |

EXAMPLE 7

Assays for Inhibition of the Angiotensin-Converting Enzyme (Cushman Article)

The inhibition studies employed a spectrophotomeric assay which measures the amount of hippuric acid produced by hydrolysis of hippuryl-L-histidyl-L-leucine, a synthetic converting enzyme substrate. Venom fractions are incubated for 3 hours at 37°C in a 0.5 ml assay mixture containing 0.1 M potassium phosphate buffer, pH 6.8, 1% NaCl, $5 \times 10^{-4}$ M hippurylhishdyllencine, and 200 μg of a 70-fold purified dog lung converting enzyme preparation. After acidification with 0.5 ml of 1.0 N HCl, the mixture is extracted with 1 ml of n-octyl alcohol and the amount of hippuric acid formed is determined from the absorbance at 235 mμ of the octanol layer. Hippuric acid and hippurylhistidylleucine have equal extinction at 235 mμ, but a much greater amount of hippuric acid is extracted into N-octanol ($\epsilon_{235}$ after extraction=3.4 mM$^{-1}$cm$^{-1}$). For determination of $I_{50}$ values the venom fractions are usually added to the assay mixtures at final concentrations of 0.1, 0.5, 2.0, 10.0 and 50 μg/ml and the percent of converting enzyme activity is plotted vs the $\log_{10}$ of the concentration of the venom fraction to determine the concentration yielding 50% inhibition. The results are as recorded in the above examples.

EXAMPLE 8

Biological assays based on the converting enzyme -catalyzed conversion of [Asp]$^1$, [Ile]$^5$ - angiotensin I to angiotensin II, as determined by contraction of the isolated rat colon, are performed in a similar manner. The assay mixture is identical except that the angiotensin I is added at $1.0 \times 10^{-4}$ M and the enzyme at 10 μg/0.5 ml; the mixture is incubated 40 minutes and stopped by boiling.

The fractions that show inhibitory activity in these assays are also able to inhibit the hypertensive response of angiotensin I in rats, in the dose range of 1–5 mg/kg. The results are as set forth in the above examples.

EXAMPLE 9

L-Pyroglutamyl-L-tryptophyl-L-prolyl-L-arginyl-L-prolyl-L-glutaminyl-L-isoleucyl-L-prolyl-L-proline A.
L-Prolyl-L-glutaminyl-L-isoleucyl-L-prolyl-L-proline The title compound is prepared starting with tert.-butyloxycarbonyl-proline polystyrene resin (8 g) containing ca. 0.5 meq. of proline per gram and is allowed to stir overnight with dichloromethane. The dichloromethane is removed by filtration and the resin is treated as follows:

1. Wash 4 times with dichloromethane (50 ml each wash), 4 times with ethanol (50 ml each wash), and 4 times with acetic acid (50 ml each wash).
2. Wash once with 1 N HCl in acetic acid (50 ml) for 5 minutes, and wash again for 25 minutes (50 ml).
3. Wash 4 times wiith acetic acid (50 ml each wash), 4 times with absolute ethanol (50 ml each wash), and 4 times with chloroform (50 ml each wash).
4. Wash twice with 50 ml of a mixture containing 3.2 ml of triethylamine in 50 ml of chloroform.
5. Wash 4 times with chloroform (50 ml each wash) and 4 times with dichloromethane (50 ml each wash).
6. Couple with tert.-butyloxycarbonyl-L-proline (7.5 mmoles) and dicyclohexylcarbodiimide (7.5 mmoles) in dichloromethane (39 ml).
7. Repeat steps 1–6, inclusive, but employing tert.-butyloxycarbonyl-L-isoleucine (7.5 mmoles) in step 6.
8. Repeat steps 1–6, inclusive, but employing tert.-butyloxycarbonyl-L-glutamine (7.5 mmoles) in step 6.

The tetrapeptide resin is next shaken with a solution of tert. butyloxycarbonyl-L-proline (2.57 g) in dichloromethane (56 ml) for 20 minutes. A solution of dicyclohexylcarbodiimide (2.5 g) in dichloromethane is added and the shaking continued for 3 hours.

The resulting pentapeptide resin is then suspended in trifluoroacetic acid (100 ml). Hydrogen bromide is bubbled hrough while cooling the flask in an ice-water mixture. After 35 minutes, the resin is filtered off and washed twice with trifluoroacetic acid and four times with a mixture of trfluoroacetic acid and dichloromethane (1:1). The combined filtrates are evaporated to dryness and the residue triturated with ether. The solid is filtered and dried to yield the free pentapeptide.

B.
L-Arginyl-L-prolyl-L-glutaminyl-L-isoleucyl-L-prolyl-L-proline

The free pentapeptide from part A is coupled with benzyloxycarbonyl-L-nitroarginine 2,4-dinitrophenyl ester at room temperature. After 1 hour triethylamine (2 ml) is added and the mixture stored at room temperature overnight. Dimethylaminopropylamine (2 ml) is added and after 1 hour the reaction mixture is concentrated at ⅛ of its original volume, diluted with ethyl acetate (1200 ml) and washed twice with 20% citric acid, once with water, and 3 times with water. After drying with sodium sulfate, the ethyl acetate is removed in vacuo to a heavy oil that solidifies upon trituration with ether (500 ml). The solid is filtered, washed with ether and dried.

The resulting benzyloxycarbonylnitro-L-arginyl-L-prolyl-L-glutaminyl-L-iosleucyl-L-prolyl-L-proline is dissolved in trifluoroacetic acid (150 ml) and the solution kept at room temperature for 1 hour. The solution is concentrated to 30 ml in vacuo and one liter of ether is added. The precipitate is filtered, washed with ether and dried in vacuo. The protected hexapeptide acid (20.3 g) is dissolved in a mixture of methanol (800 ml), water (400 ml) and N HCl (46 ml) and hydrogenated with 10% palladium on charcoal (4 g) for 20 hours. The completion of hydrogenolysis is ascertained by the disappearance of the UV absorption at 270 mμ. The catalyst is removed by filtration and the filtrate concentrated in vacuo. The residue is dissolved in methanol (70 ml) and added to ether (1.5 liter) with vigorous stirring. The precipitate is filtered and washed with ether.

C. L-Pyroglutamyl-L-tryptophyl-L-proline e

Proline tert.-butyl ester (0.80 g) and tert.-butyloxycarbonyl tryptophane 2,4,5-trichlorophenyl ester (2.38 g) are dissolved in a mixture of 20 ml of dichloromethane and 1 ml of dimethylformamide (DMF). After 24 hours, the reaction mixture is diluted with dichloromethane, washed with aqueous acid and base and the solvent evaporated in vacuo. The residue is dissolved in trifluoroacetic acid. After one hour at room temperature the solvent is removed in vacuo. The residue is triturated with ether until solidification.

The above dipeptide (1.2 g) and pyroglutamic acid 2,4,5-trichlorophenyl ester (1.1 g) are dissolved in a mixture of 0.5 ml of triethylamine (TEA) and DMF (15 ml). After 16 hours at room temperature, the solvent is removed in vacuo, the residue dissolved in isopropanol and the solution poured into diisopropyl ether with stirring. The solid precipitate is filtered and washed with isopropyl ether.

D. L-Pyroglutamyl-L-tryptophyl-L-prolyl-L-arginyl-L-prolyl-L-glutaminyl-L-isoleucyl-L-prolyl-L-proline The tripeptide, from part C, Pyr-Trp-Pro (23.3 mmoles) is dissolved in DMF (85 ml) and 3.27 ml (23.3 mmoles) TEA, the solution cooled to −20° (inside the flask, or −35° to −40° in the cooling bath) and kept at this temperature for 15–20 minutes. To this cold solution 3.19 ml of isobutyloxycarbonyl chloride is added and then a time of 30 minutes is allowed for the mixed anhydride to be formed at the same temperature. A solution of Arg-Pro-Gln-Ile-Pro-Pro (16.5 g) in DMF (100 ml) is precooled to about 0° and then added into the solution of the mixed anhydride. At this moment, the pH value is adjusted to 8 with TEA (8.5 ml) while the temperature of 0° is maintained. After 20 to 24 hours at room temperature, the volume of the solvents is reduced to ⅓–¼ and poured into 20–25 volumes of EtOAc containing 3 % of AcOH. The precipitate is washed thoroughly with EtOAc and then dried in vacuo over KOH overnight to yield the title compound. This material is dissolved in water, sterilized by filtration, and the sterile aqueous solution freeze-dried to a free flowing powder. The powder is reconstituted for injection with water for injection or saline.

What is claimed is:

1. A method of inhibiting the enzymatic conversion of angiotensin I into angiotensin II which comprises contacting angiotensin I with an effective amount of the nonapeptide L-pyroglutamyl-L-tryptophyl-L-prolyl-L-arginyl-L-prolyl-L-glutaminyl-L-isoleucyl-L-prolyl-L-proline.

2. A method according to claim 1 wherein the concentration of the nonapeptide is from about 0.05 to about 10 μg/ml.

3. A method of inhibiting the hypertensive effect of angiotensin I in mammalian species which comprises administering by injection to the mammal from about 0.025 mg/kg to about 4 mg/kg of L-pyroglutamyl-L-tryptophyl-L-prolyl-L-arginyl-L-prolyl-L-glutaminyl-L-isoleucyl-L-prolyl-L-proline.

4. Lyophilized L-pyroglutamyl-L-tryptophyl-L-prolyl-L-arginyl-L-prolyl-L-glutaminyl-L-isoleucyl-L-prolyl-L-proline reconstituted with water or saline for injection in mammals to inhibit the hypertensive effect of angiotensin I.

5. A sterile injectable solution for use in inhibiting the hypertensive effect of angiotensin I, comprising the nonapeptide L-pryroglutamyl-L-tryptophyl-L-prolyl-L-arginyl-L-prolyl-L-glutaminyl-L-isoleucyl-L-prolyl-L-proline and water for injection or saline in a concentration at least sufficient to dissolve the nonapeptide.

* * * * *

UNITED STATES PATENT AND TRADEMARK OFFICE
CERTIFICATE OF CORRECTION

PATENT NO. : 3,947,575
DATED : March 30, 1976
INVENTOR(S) : Miguel A. Ondetti

It is certified that error appears in the above-identified patent and that said Letters Patent are hereby corrected as shown below:

Column 2, line 34, "dextranmolecular" should read
  --dextran molecular--.
Column 4, line 44, "ammmonium" should read --ammonium--.
Column 7, line 22, "hippurylhishdyl" should read
  --hippurylhistidyl--.
Column 7, line 23, "lencine" should read --leucine--.
Column 8, line 28, "hrough" should read --through--.
Column 9, line 1, delete the "e" at the end of the line.

Signed and Sealed this

Twenty-first Day of September 1976

[SEAL]

Attest:

RUTH C. MASON
Attesting Officer

C. MARSHALL DANN
Commissioner of Patents and Trademarks